(12) United States Patent
Brown

(10) Patent No.: US 9,345,543 B2
(45) Date of Patent: May 24, 2016

(54) LASER DELIVERY APPARATUS FOR ENDOVASCULAR APPLICATIONS

(76) Inventor: Joe Denton Brown, Panama City, FL (US)

( * ) Notice: Subject to any disclaimer, the term of this patent is extended or adjusted under 35 U.S.C. 154(b) by 1809 days.

(21) Appl. No.: 12/496,905

(22) Filed: Jul. 2, 2009

(65) Prior Publication Data

US 2010/0004646 A1 Jan. 7, 2010

Related U.S. Application Data

(60) Provisional application No. 61/129,518, filed on Jul. 2, 2008.

(51) Int. Cl.
*A61B 18/22* (2006.01)
*A61B 18/24* (2006.01)

(52) U.S. Cl.
CPC ............... *A61B 18/24* (2013.01); *A61B 18/245* (2013.01); *A61B 2018/2272* (2013.01)

(58) Field of Classification Search
USPC ....................................... 606/7–9; 607/88, 89
See application file for complete search history.

(56) References Cited

U.S. PATENT DOCUMENTS

| | | | |
|---|---|---|---|
| 4,385,832 A | 5/1983 | Doi et al. | |
| 4,519,390 A | 5/1985 | Horne | |
| 4,543,477 A | 9/1985 | Doi et al. | |
| 4,669,465 A | 6/1987 | Moore et al. | |
| 4,718,417 A | 1/1988 | Kittrell et al. | |
| 4,760,845 A | 8/1988 | Kovalcheck | |
| 4,832,024 A | 5/1989 | Boussignac et al. | |
| 4,883,054 A | 11/1989 | Fuller et al. | |
| 4,913,142 A | 4/1990 | Kittrell et al. | |
| 4,994,059 A | 2/1991 | Kosa et al. | |
| 5,057,099 A | 10/1991 | Rink | |
| 5,061,265 A | 10/1991 | Abela et al. | |
| 5,098,427 A | 3/1992 | Hessel et al. | |
| 5,154,707 A | 10/1992 | Rink et al. | |
| 5,196,005 A | 3/1993 | Doiron et al. | |
| 5,219,345 A | 6/1993 | Potter | |
| 5,300,066 A | 4/1994 | Manoukian et al. | |
| 5,330,465 A | 7/1994 | Doiron et al. | |
| 5,354,323 A | 10/1994 | Whitebook | |
| 5,569,240 A | 10/1996 | Dowlatshahi et al. | |
| 5,649,923 A | 7/1997 | Gregory et al. | |
| 5,820,627 A | 10/1998 | Rosen et al. | |
| 5,928,222 A | 7/1999 | Kleinerman | |
| 5,968,033 A | 10/1999 | Fuller et al. | |
| 6,389,307 B1 | 5/2002 | Abela | |
| 6,398,777 B1 | 6/2002 | Navarro et al. | |
| 6,981,971 B2 | 1/2006 | Caldera et al. | |
| 2002/0013574 A1* | 1/2002 | Elbrecht et al. | 606/5 |
| 2002/0045811 A1 | 4/2002 | Kittrell et al. | |
| 2002/0068963 A1 | 6/2002 | Maki et al. | |
| 2003/0023236 A1 | 1/2003 | Gowda et al. | |
| 2004/0006333 A1 | 1/2004 | Arnold et al. | |
| 2004/0092913 A1 | 5/2004 | Hennings et al. | |
| 2004/0147912 A1 | 7/2004 | Sinofsky | |
| 2004/0147913 A1 | 7/2004 | Sinofsky | |
| 2004/0162490 A1 | 8/2004 | Soltz et al. | |
| 2004/0249261 A1 | 12/2004 | Torchia et al. | |

(Continued)

*Primary Examiner* — William Thomson
*Assistant Examiner* — Jeffrey Lipitz
(74) *Attorney, Agent, or Firm* — Bacon & Thomas, PLLC

(57) ABSTRACT

An apparatus for delivering energy, and in particular laser energy, to a tissue includes a protective quartz cap that is secured to a laser delivery fiber by a crimp sleeve. The fiber may have a conical tip, and the quartz cap may be secured to the crimp sleeve by a layer of epoxy.

12 Claims, 1 Drawing Sheet

(56) References Cited

U.S. PATENT DOCUMENTS

| | | |
|---|---|---|
| 2005/0038419 A9 | 2/2005 | Arnold et al. |
| 2005/0124985 A1 | 6/2005 | Takayama et al. |
| 2005/0131400 A1* | 6/2005 | Hennings et al. .............. 606/15 |
| 2005/0267452 A1 | 12/2005 | Farr et al. |
| 2005/0273090 A1 | 12/2005 | Nieman et al. |
| 2005/0288654 A1 | 12/2005 | Nieman et al. |
| 2005/0288655 A1 | 12/2005 | Root et al. |
| 2006/0052661 A1 | 3/2006 | Gannot et al. |
| 2006/0122587 A1 | 6/2006 | Sharareh |
| 2006/0217692 A1 | 9/2006 | Nauberger |
| 2006/0217693 A1 | 9/2006 | Gowda et al. |
| 2006/0253178 A1 | 11/2006 | Masotti |
| 2007/0049911 A1 | 3/2007 | Brown |
| 2007/0167937 A1 | 7/2007 | Brown |

* cited by examiner

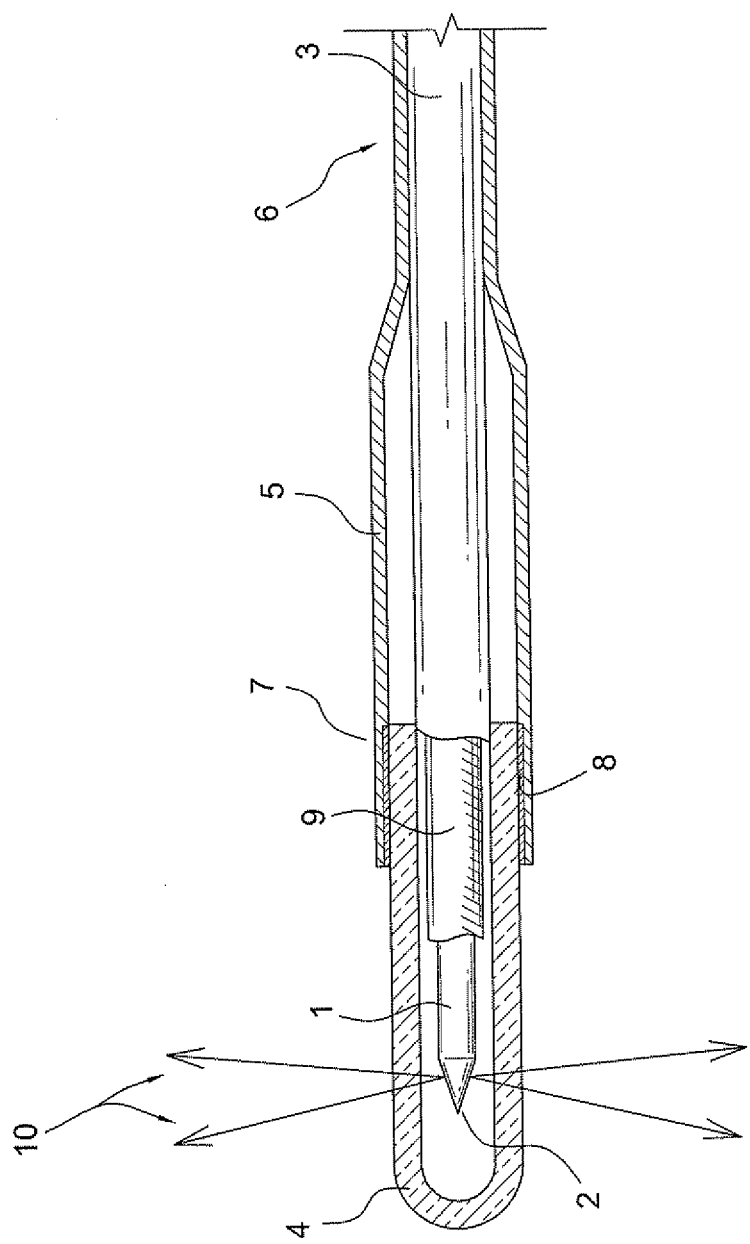

LASER DELIVERY APPARATUS FOR ENDOVASCULAR APPLICATIONS

This invention claims the benefit of U.S. Provisional Patent Application Ser. No. 61/129,518, filed Jul. 2, 2008.

BACKGROUND OF THE INVENTION

This invention relates to an improvement over the laser delivery arrangement described in U.S. patent application Ser. No. 11/714,785, filed Aug. 28, 2006, which was published on Mar. 21, 2007, as U.S. Published Patent Application No. 2007-1067937, and is incorporated herein by reference.

The prior application discloses a laser delivery arrangement in which a Teflon™ introducer extends beyond the tip of the fiber and thereby prevents contact between the fiber tip and the wall of a blood vessel or other tissue being treated. The tip of the fiber is arranged to direct laser light in a radial direction so as to impinge on walls of the vessel. One example of a suitable fiber tip is a conical tip, which is also the type of tip illustrated herein, although it will be appreciated that other fiber tip configurations may be substituted for the illustrated fiber tip, and that the invention is not limited to a particular type of optical fiber.

DESCRIPTION OF PREFERRED EMBODIMENT

The improvement provided by the present invention is to replace the Teflon™ introducer with a quartz cap that is secured to the end of the fiber by a metal crimp sleeve.

An example is illustrated in FIG. 1, which shows a fiber having a silicon core 1, conical tip 2, Teflon™ buffer 3, and cladding layer 9. The conical tip 3 directs laser energy supplied by the fiber in a generally radial direction though a quartz cap 4, which is secured to the Teflon™ buffer 3 by a metal crimp sleeve 5 that is crimped to the buffer at one end 6, and that is secured to the quartz cap at a second end 7 by a layer of epoxy 8. The generally radial laser output is indicated by reference numeral 10.

In order to prevent thermal runaway to the quartz cap, a preferred method of using the arrangement illustrated in FIG. 1 is to modulate the laser output during treatment of a tissue, for example by moving the fiber back and forth.

The quartz cap arrangement described herein may advantageously be used with safety feedback arrangements of the type disclosed in copending U.S. patent application Ser. No. 11/510,691, filed Aug. 28, 2006 (Pub. No. 2007/0049911, Mar. 1, 2007); Ser. No. 11/714,785, filed Mar. 7, 2002 (Pub. No. 2007/0049911, Mar. 1, 2007); and Ser. No. 12/047,819, filed Mar. 13, 2008 (Pub. No. 2009/0062782, Mar. 5, 2009) to ensure that damage is minimized or prevented should overheating occur despite the modulation. The copending applications are incorporated herein by reference.

Use with a safety feedback arrangement involves monitoring a temperature of the treatment site or radiation emitted during treatment in order to prevent damage due to overheating. As explained in the copending applications, different wavelengths of radiation may be monitored, including but not limited to visible light, and the monitoring may be carried out either by detectors at or near the treatment site or by transmitting the radiation back through the fiber.

Having thus described preferred embodiments of the invention in sufficient detail to enable those skilled in the art to make and use the invention, it will nevertheless be appreciated that variations and modifications of the illustrated embodiment may be made without departing from the spirit of the invention.

For example, different fibers may be substituted for the illustrated silicon core/Teflon™ buffer fiber, so long as the quartz cap can be secured thereto by a crimp sleeve. In addition, the crimp sleeve need not necessarily be made of metal, and the adhesive used to secure the quartz cap need not necessarily be epoxy. For example, adhesive materials other than epoxy may be substituted for epoxy layer 8, and the metal crimp sleeve may alternatively be secured to the quartz cap by mechanical means, by welding, or by any other metal-to-quartz joining method or material.

Still further, the crimp sleeve may be made of a material other than metal, transparent materials other than quartz may used in the cap, and the conical tip may be replaced by other tips such as the alternative tips disclosed in U.S. patent application Ser. No. 11/510,691, including orb-shaped, inverted cone-shaped, and angled tips, as well as tips with separate reflective structures such as the one shown in FIG. 4E of U.S. patent application Ser. No. 11/510,691.

In addition, the arrangement of the preferred embodiments may be used with feedback arrangements other than those disclosed in U.S. patent application Ser. Nos. 11/510,691; 11/714,785; and Ser. No. 12/047,819, cited above, or without feedback, and in a wide variety of applications, including but not limited to endovascular applications.

It is therefore intended that the invention not be limited by the above description or accompanying drawings, but that it be defined solely in accordance with the appended claims.

What is claimed is:

1. An arrangement for preventing contact between a laser delivery fiber and a tissue, said fiber including a core and a buffer, said arrangement comprising:
   a crimp sleeve; and
   a transparent cap secured to said crimp sleeve and surrounding a tip of said fiber,
   wherein laser energy is directed by said tip of said fiber through said transparent cap to said tissue, and
   wherein said crimp sleeve is crimped to said buffer.

2. An arrangement as claimed in claim 1, wherein said crimp sleeve is a metal sleeve.

3. An arrangement as claimed in claim 2, wherein said transparent cap is a quartz cap.

4. An arrangement as claimed in 3, wherein said quartz cap is secured to said crimp sleeve by an epoxy layer.

5. An arrangement as claimed in claim 1, wherein said transparent cap is a quartz cap.

6. An arrangement as claimed in claim 5, wherein said quartz cap is secured to said crimp sleeve by an epoxy layer.

7. An arrangement as claimed in claim 1, wherein said transparent cap is secured to said crimp sleeve by an epoxy layer.

8. An arrangement as claimed in claim 1, wherein said tip of said fiber is a conical tip.

9. A method of using the fiber of claim 1, comprising the step of modulating the laser energy during treatment.

10. A method as claimed in claim 9, wherein the modulating step is carried out by moving the fiber back-and-forth during treatment.

11. A method as claimed in claim 10, further comprising the step of monitoring a temperature of the treatment site or radiation emitted during treatment in order to prevent damage due to overheating.

12. A method of using the fiber of claim 1, comprising the step of monitoring a temperature of the treatment site or radiation emitted during treatment in order to prevent damage due to overheating.

* * * * *